(12) United States Patent
Krenzel

(10) Patent No.: US 8,733,365 B2
(45) Date of Patent: May 27, 2014

(54) IMMOBILIZER

(76) Inventor: Ronald Louis Krenzel, Longmont, CO (US)

(*) Notice: Subject to any disclaimer, the term of this patent is extended or adjusted under 35 U.S.C. 154(b) by 0 days.

(21) Appl. No.: 13/493,001

(22) Filed: Jun. 11, 2012

(65) Prior Publication Data

US 2012/0245498 A1 Sep. 27, 2012

Related U.S. Application Data

(62) Division of application No. 10/780,942, filed on Feb. 17, 2004, now Pat. No. 8,196,588.

(51) Int. Cl.
*A61B 19/00* (2006.01)

(52) U.S. Cl.
USPC ............... 128/869; 128/875; 128/876; 602/4; 24/303

(58) Field of Classification Search
USPC ............... 128/869, 875–876, DIG. 19, 100.1; 602/4, 20; 482/105; 24/303
See application file for complete search history.

(56) References Cited

U.S. PATENT DOCUMENTS

| | | | |
|---|---|---|---|
| 2,187,323 A | 1/1940 | Kelton et al. | |
| 2,358,551 A | 9/1944 | Beaton | |
| 3,000,378 A | 9/1961 | Zieman | |
| 3,338,236 A | 8/1967 | McLeod, Jr. | |
| 3,404,680 A | 10/1968 | Guttman et al. | |
| 3,815,588 A | 6/1974 | Klausner | |
| 3,827,716 A * | 8/1974 | Vaughn et al. | 280/730.1 |
| 4,188,944 A | 2/1980 | Augustyniak | |
| 4,598,703 A | 7/1986 | Lindemann | |
| 4,716,895 A | 1/1988 | Marques et al. | |
| 4,834,082 A | 5/1989 | Ghadiali | |
| 5,203,763 A | 4/1993 | Lajiness-O'Neill | |
| 5,358,470 A | 10/1994 | Johnson | |
| 5,358,471 A | 10/1994 | Klotz | |
| 5,403,268 A | 4/1995 | Clement | |
| 5,520,620 A | 5/1996 | Johnson | |
| 5,558,626 A | 9/1996 | Holtzman et al. | |
| 5,628,725 A | 5/1997 | Ostergard | |

(Continued)

FOREIGN PATENT DOCUMENTS

| DE | 3936232 | 5/1991 |
|---|---|---|
| EP | 0198482 | 4/1986 |

OTHER PUBLICATIONS

SupportsUSA, shoulder supports, arm slings and immobilizers; www.supoortsusa.com/arm/shoulder; Mar. 11, 2003; 3 pages.

(Continued)

*Primary Examiner* — Patricia Bianco
*Assistant Examiner* — Camtu Nguyen
(74) *Attorney, Agent, or Firm* — Sheridan Ross P.C.

(57) ABSTRACT

This invention generally relates to a product and method to restrain movement, and more particularly to a product and method to releasably restrain the movement of a part of the human body, such as an arm or a leg. In one embodiment of the invention, a first piece is releasably positioned at a part of the body the movement of which is desired to be restrained and a second piece is positioned at the desired location of restraint. The first piece and the second piece are adapted to be releasably connected to each other, such as by magnetic forces, the attractive magnetic forces of two or more magnets, or by mechanical forces such as by a snap, button, buckle, pin, hook and loop fastener or other device.

5 Claims, 9 Drawing Sheets

(56) References Cited

U.S. PATENT DOCUMENTS

| | | | |
|---|---|---|---|
| 5,682,653 | A | 11/1997 | Berglof et al. |
| 5,857,990 | A | 1/1999 | Maas |
| 5,867,826 | A | 2/1999 | Wilkinson |
| 6,099,489 | A | 8/2000 | Herzberg et al. |
| 6,106,493 | A | 8/2000 | Rozell |
| RE36,869 | E | 9/2000 | Ewen |
| 6,292,985 | B1 | 9/2001 | Grunberger |
| 6,421,834 | B2 | 7/2002 | Kester |
| 6,464,656 | B1 | 10/2002 | Salvucci et al. |
| 6,837,862 | B2 | 1/2005 | Driver |
| 6,945,945 | B2 | 9/2005 | Givler et al. |
| 7,789,114 | B2 | 9/2010 | Pace et al. |
| 8,196,588 | B1 | 6/2012 | Krenzel |

OTHER PUBLICATIONS

Frank Stubbs, Inc.; www.fstubbs.com/noflash/orthooedic/324.htm; Dec. 1, 2003; 1 page.

Manor Drug Store; www.manordrug.com/FLA/fla/products/28-911.htm; Dec. 1, 2003; 1 page.

Therafin Corporation; www.therafin.com/armposition.htm; Feb. 27, 2004; 2 pages.

Ambroise, The Wilmer® Carrying Orthosis; Wilmer® Carrying Orthosis for Brachial Plexus; www.ambroise-uk.com/carryingOrthosis.htm; Mar. 26, 2003; 1 page.

Dalco Arm Slings; www.dalcointernational.com/Dalco_Arm_Slings.html; Feb. 4, 2003; 2 pages.

Arm Slings: Universal Shoulder Immobilizer—FastHealth Sports Injury Store; www.fasthealth.com/store/motion/ortho-12-4129.php; Apr. 4, 2003; 1 page.

SupportsUSA; Super Sling—Universal Shoulder Immobilizer; http://supports4less.comfbirdcronin/shouldersupports/superslingshoulderimmobilizer.htm; Feb. 4, 2003; 1 page.

SupportsUSA; Sling and Swathe Shoulder Immobilizer; http://supports4less.com/birdcronin/shouldersupports/slingswatheshoulderimmobilizer.htm; Feb. 4, 2003; 1 page.

SupportsUSA; Comfor™ Shoulder Immobilizer. Universal; http://supports4less.com/birdcronin/shouldersupports/comforuniversal-shoulderimmobilizer . . . ; Feb. 4, 2003; 1 page.

SupportsUSA; Bicro™ Shoulder Immobilizer; http://supports4less.com/birdcronin/shouldersupports/bicroshoulderimmobilizer.htm; Feb. 4, 2003; 1 page.

Joslin Orthopedic Gear; The Ultimate Arm Sling®; Arm Sling Design; www.armsling.com/design.htm; Februay 8, 2003; 2 pages.

Office Action for U.S. Appl. No. 10/780,942, mailed Mar. 17, 2006, 5 pages.

Office Action for U.S. Appl. No. 10/780,942, mailed Jun. 14, 2006, 6 pages.

Office Action for U.S. Appl. No. 10/780,942, mailed Feb. 21, 2008, 5 pages.

Office Action for U.S. Appl. No. 10/780,942, mailed Jun. 17, 2009, 9 pages.

Final Office Action for U.S. Appl. No. 10/780,942, mailed Apr. 26, 2010, 9 pages.

Office Action for U.S. Appl. No. 10/780,942, mailed May 11, 2011, 10 pages.

Final Office Action for U.S. Appl. No. 10/780,942, mailed Oct. 11, 2011, 12 pages.

Advisory Action for U.S. Appl. No. 10/780,942, mailed Feb. 24, 2012, 3 pages.

Notice of Allowance for U.S. Appl. No. 10/780,942, mailed Mar. 14, 2012, 7 pages.

* cited by examiner

IMMOBILIZER

This application is a divisional of U.S. patent application Ser. No. 10/780,942, filed Feb. 17, 2004, now U.S. Pat. No. 8,196,588, the entire disclosure of which is incorporated by reference herein.

FIELD OF INVENTION

This invention generally relates to a product and method to restrain movement, and more particularly to a product and method to releasably restrain the movement of a part of the human body, such as an arm or a leg.

BACKGROUND

Various devices have been used to limit movement of parts of the human body for various purposes, such as allowing an injury to heal. In the case of immobilizing an arm or a shoulder, a common device is the shoulder sling. In general, a shoulder sling uses a swath of material to encircle and cradle the lower part of the arm. A length of material, such as a strap, is attached at one end of the swath of material, is looped around the neck of the user and is attached at the other end of the swath of material. The strap then holds the swath of material, which holds the arm in a desired position.

The length of a strap in a typical sling may be adjusted somewhat to allow the arm to be positioned within a certain range of angles. In general, as the length of the strap is increased, the position of the arm relative to the torso is lowered. However, the range of positions is limited by the structure of the sling itself.

Existing slings are typically worn over the outside of clothing and are very visible to others. If existing slings are worn under an article of clothing, the arm being held in the sling also is positioned under that article of clothing. Also, immobilizers for legs typically involve straps with cumbersome mechanical attachment mechanisms, such as buckles and cinches. In any event, the slings and other existing immobilizers are cumbersome to use, offer a limited range of positions and are otherwise limited in their use. Further, slings and other existing immobilizers typically do not allow for particularized motion, e.g., restraining the movement of the upper arm while allowing significant use of the hand.

As such, a need exists for an improved product and method to restrain movement, such as movement of a part of the human body, that is more simple, easier to use, less cumbersome, less visible, adaptable to allow particularized motion and more secure while being more easily releasable.

DETAILED DESCRIPTION

Figure 1:
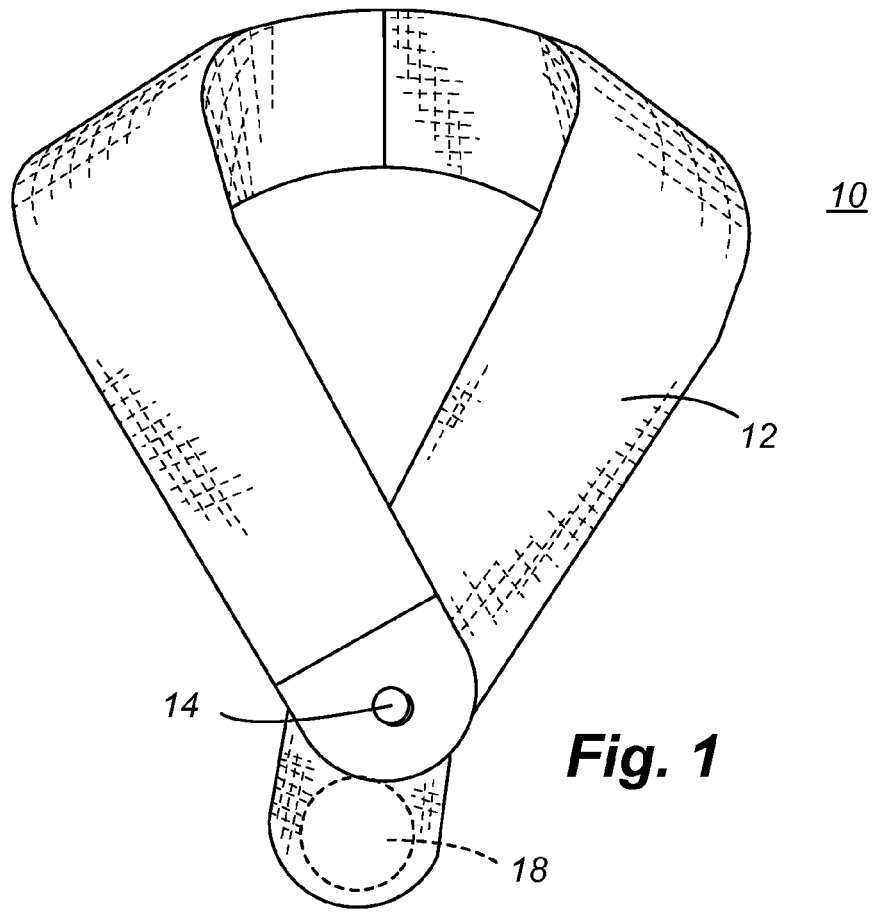
FIG. 1 depicts a front perspective view of one embodiment of the invention comprising a harness containing a magnetic device.

The invention generally relates to a product and method to restrain movement, and more particularly to a product and method to releasably restrain the movement of a part of the human body, such as an arm or a leg.

In one embodiment of the invention, magnetic forces are employed to releasably connect at least one magnetic device positioned at a part of the body, such as an arm or leg, to at least one other magnetic device positioned at another part of the body or positioned at another structure. A first magnetic device is positioned at or near the part of the human body the movement of which is desired to be restrained and a second magnetic device is positioned at the desired location of restraint, which may be at another portion of the user's body or a separate structure. The attractive magnetic forces of the two magnets operate to releasably attach the two magnets to each other and to releasably immobilize, secure and/or support the part of the body at the desired position. The product and method of the present invention may be adapted to restrain the movement of and/or support one or both arms, one or both legs, the head, the neck, the torso, other body parts, various combinations thereof, and even the entire body.

Through the use of a product and method of the invention, a human arm may be temporarily and releasably restrained in movement and/or supported in a desired position, e.g., for facilitating the healing of an injury, for immobilizing the arm to inhibit interference with medical or other attention to other parts of the body, or for supporting an arm weakened by injury, disability or disease, such as a stroke or Parkinson's Disease, among many other things. For example, a first magnet may be positioned on the arm, preferably at or near the forearm or wrist, and a second magnet may be positioned at a desired location, such as a desired position along the torso of the user. The attractive forces between the two magnets operate to releasably attach the two magnets to one another. The arm is thereby temporarily restrained in movement, held in a desired position and supported. Some, most, substantially all, or even all of the device may be concealed under the user's clothing during use.

One embodiment of the invention comprises a strap containing one or more magnetic devices and harness containing one or more magnetic devices. The strap preferably is adapted to be releasably and adjustably attached to part of an arm, while the harness preferably is adapted to be releasably and adjustably attached to at least a part of the torso of the user.

More specifically, the harness of this embodiment is adapted to secure the one or more magnets in a desired location and to contain one or more devices to magnetically attract the magnet contained in the strap. In the embodiment of the invention shown in FIG. 1, a harness 10 comprises a neck loop 12, one end of which is releasably attachable by connector 14, and at least one magnet 18.

The neck loop 12 is adapted to extend around the neck of a person, with the neck loop 12 preferably releasably attachable by connector 14 to facilitate the positioning of the harness 10 on the user. Neck loop 12 is of sufficient strength to support the harness and the arm when in use, while being sufficiently flexible for comfortable use. The neck loop 12 may be constructed of a variety of materials, such as natural fabrics, synthetic fabrics, plastics, and combinations thereof, and preferably is constructed of a foam material covered by a woven synthetic laminated nylon fabric.

Neck loop 12 is of sufficient length to encircle the neck of the user and preferably is approximately 24 inches to approximately 36 inches in length. For increased support and comfort, neck loop 12 also preferably is contoured to generally follow the contour of a user's neck and/or shoulder. Even more preferably, neck loop 12 is constructed of two pieces of material sewn together to form the contoured shape. As shown in FIG. 1, neck loop 12 more preferably has a width at each end that is less than the width in the middle, where the neck loop 12 is intended to contact the neck and/or shoulder area of the user.

The connector 14 may be any number of mechanisms to releasably attach one or both ends of neck loop 12 to close the loop around the neck of the user, such as a button, buckle, pin, hook and loop fastener, or similar device, and preferably is a snap. Alternatively, neck loop 12 may be a closed loop that is not readily opened or opened at all, but rather is sufficiently large to slip over the head of a user.

The strap is designed to hold or secure at least one magnet at a desired location, such as along an arm or leg. Preferably, the strap is a length of material designed to wrap around the arm or leg and be secured with a releasable fastener, such as a button, buckle, snap, hook and loop fastener or similar device. More preferably, the length of strap may be adjustable to securely wrap around varying dimensions of arms and legs, and be secured to the desired degree of snugness with the releasable fastener. For example, the dimensions of arms and legs vary between individuals and even within the same individual, e.g., depending on the thickness of any clothing being worn by the individual under the strap, the existence and thickness of a cast, or other material affecting the circumference of the arm or leg. Alternatively, the strap may be a closed loop that is not readily opened or opened at all, but rather is sufficiently large to slip over the desired body part or parts.

The strap preferably is of sufficient dimensions to contain the desired number and size of magnets for the desired application. For a strap designed to be wrapped around a forearm or wrist, preferably the strap is approximately 2 inches to approximately 8 inches wide and approximately 10 inches to approximately 20 inches long to allow use for a variety of shapes and sizes of wrists, forearms, upper arms, etc., with or without extra clothing, casts and other material. For a strap designed to be wrapped around a leg, preferably the strap is approximately 2 inches to approximately 8 inches wide and approximately 14 inches to approximately 30 inches long to allow use for a variety of shapes and sizes of ankles, calves, thighs, etc. Straps designed to be used in other applications should be of sufficient width and length to releasably attach the strap to the desired body part and to hold at least one magnet at the desired location.

The strap may be constructed of a wide variety of materials, such as natural fabrics, synthetic fabrics, plastics, and combinations thereof, and preferably is constructed of a relatively elastic, woven fabric, and with at least some foam material for increased comfort. In a preferred embodiment, the material covers substantially all of the magnet, such that in operation the two attractive magnets are not in direct metal-to-metal contact with each other. Preferably, such a material covering the magnet is a woven fabric.

The strap is designed to contain one or more magnets, and preferably one magnet. The one or more magnets may be held on or within the strap in a variety of ways, including readily removable means such as within an open sleeve or a closable sleeve, or preferably less readily removable means such as a sewn-in enclosure.

More than one strap, each containing at least one magnet, may be used. In the embodiment of an arm immobilizer, preferably one strap containing one magnet is used, which typically will be sufficient to securely hold the magnet in the desired location and to immobilize the arm when magnetically attached to the corresponding magnet secured at the desired location. A single strap with a single magnet generally is more simple to manufacture, more cost effective and more simple to use. In the embodiment of a leg immobilizer, one, two, three, or more straps may be advantageously employed, depending on the length of leg desired to be restrained in movement and the degree of restraint desired. For an application of temporarily restraining the movement of a leg while the user is in a wheelchair, preferably one strap is wrapped around the leg of the user, at or near the ankle. In embodiments of the invention designed to immobilize more than one limb or much or all of the body, e.g., in a hospital bed, multiple straps or other devices may be used at various positions, each containing one or more magnets to correspond to an attractive magnet on the support structure, such as a part of or attachment to the hospital bed.

Figure 2:
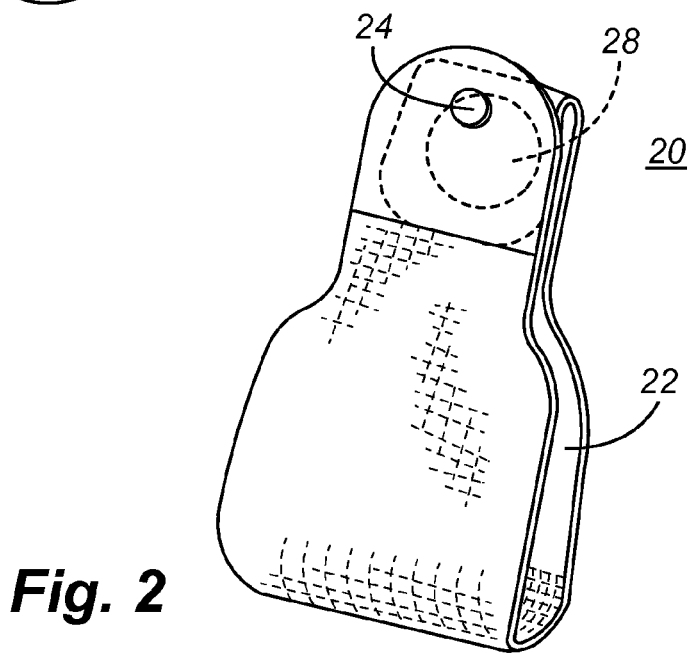
FIG. 2 depicts a front perspective view of one embodiment of the invention comprising a strap containing a magnetic device.

In the embodiment depicted in FIG. 2, a strap 20 comprises a length of material forming closable loop 22, snap connector 24 and at least one magnet 28. Strap 20 is sized and shaped to wrap around a portion of the arm of the user.

Figure 3:
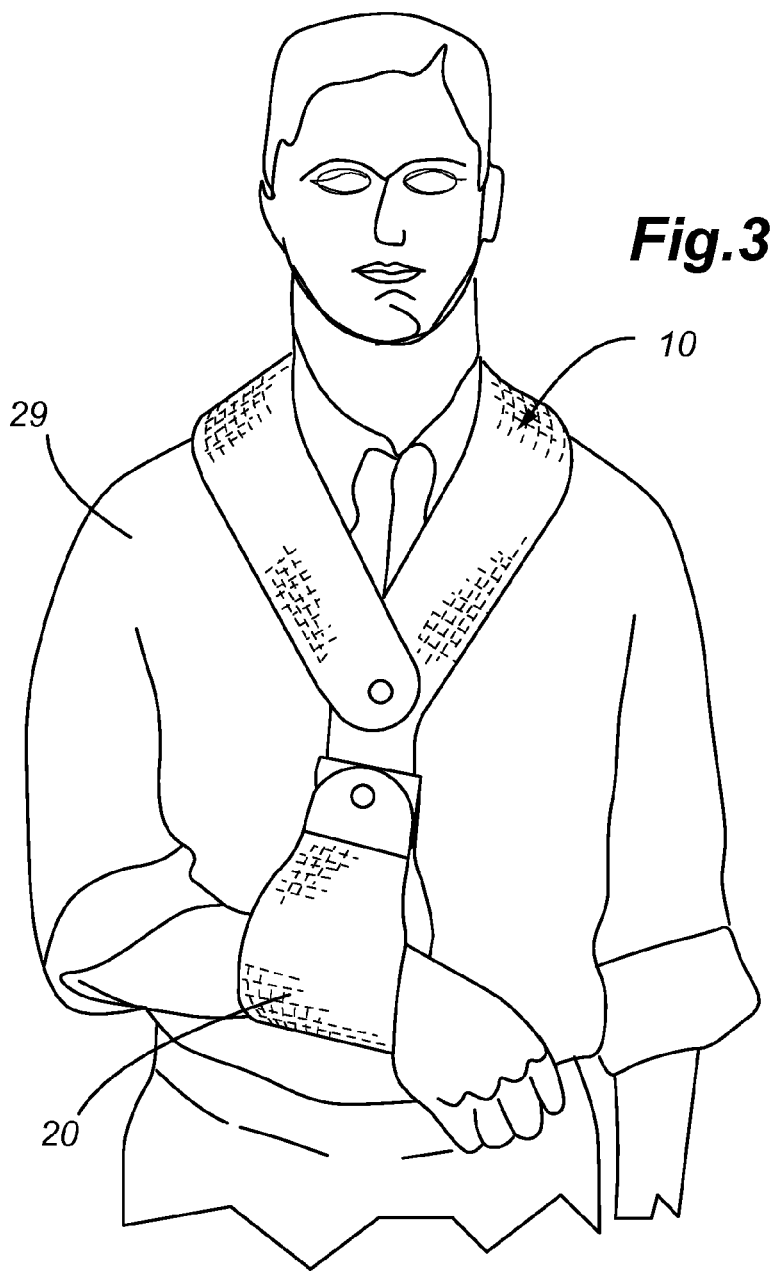
FIG. 3 depicts a front perspective view of the harness of FIG. 1 and the strap of FIG. 2 as utilized by a person.

Referring now to FIG. 3, the harness 10 depicted in FIG. 1 and the strap 20 depicted in FIG. 2 are illustrated in use on the body of user 29. The harness 10 has been positioned around the neck of the user 29 and closed to form a loop. The strap 20 has be positioned around the forearm of the user 29 and closed to form a loop. The magnet 18 of harness 10 and the magnet 28 of strap 20 are releasably attached by attractive magnetic forces after positioning them in close proximity to each other.

Figure 4:
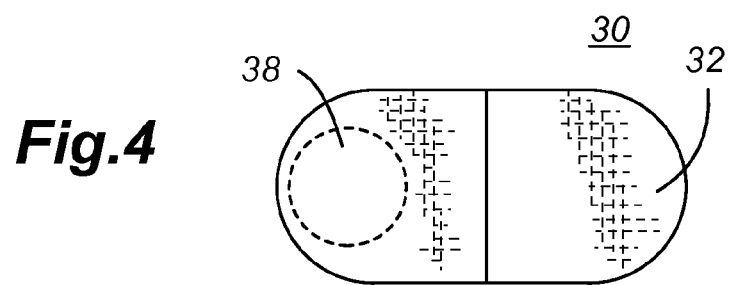
FIG. 4 depicts a front view of another embodiment of the invention comprising a magnet holder and a magnet.
Figure 12:
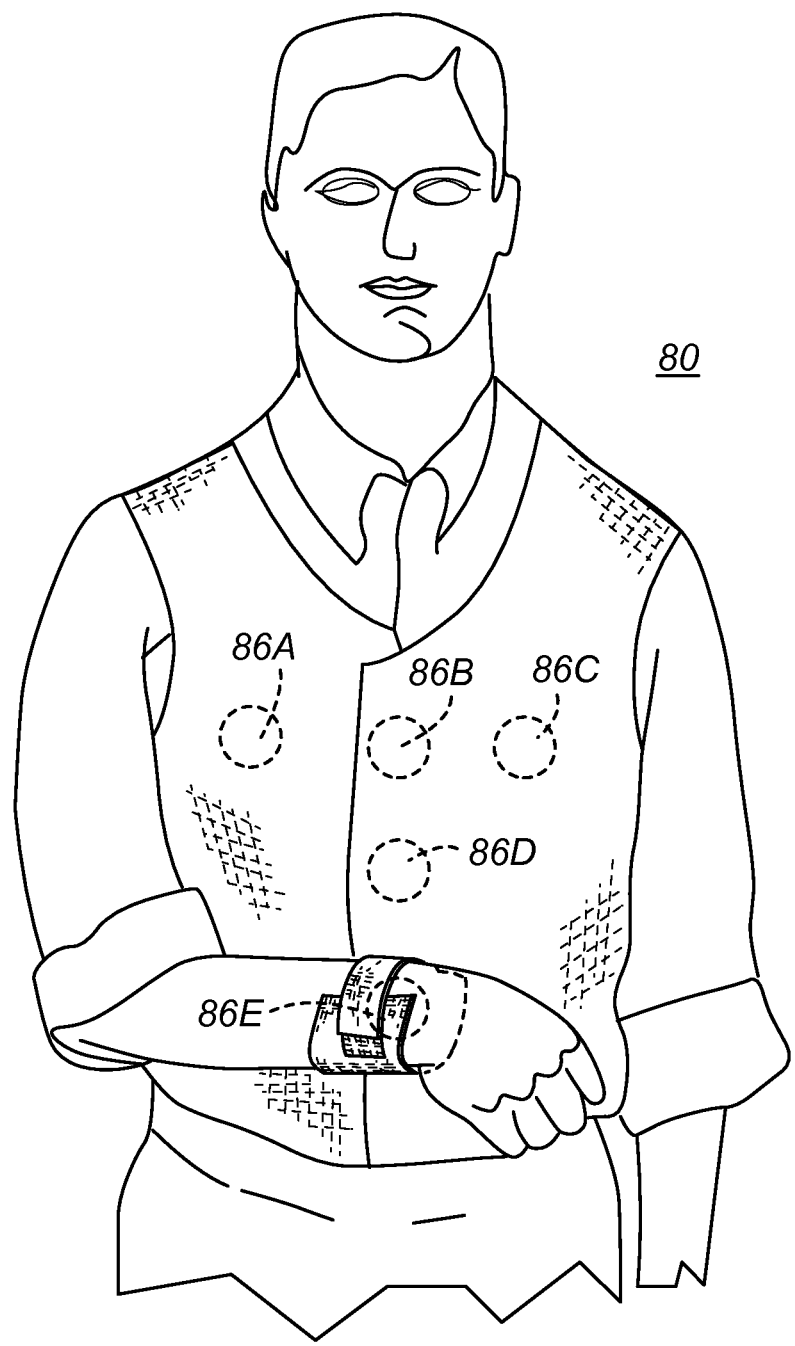
FIG. 12 depicts yet another embodiment of the invention comprising an article of clothing containing one or more magnetic devices and a strap as utilized by a person.

An alternative embodiment of the invention is depicted in FIG. 4, which depicts a magnet holder 30 designed for use in place of, or in combination with, a harness, such as the harness 10 of FIG. 1 or the article of clothing 80 of FIG. 12. Referring now to FIG. 4, a magnet holder 30 comprises a length of material 32 and at least one magnet 38. The magnet holder 30 is sized sufficiently to hold at least one magnet 38 and preferably is sufficiently large for a user to grasp, hold and maneuver the magnet holder 30 to the desired position. Preferably, magnet holder 30 is approximately 1 inch to approximately 3 inches wide and approximately 2 inches to approximately 6 inches long. The magnet holder 30 may be constructed of a variety of materials, including natural fabrics, synthetic fabrics, plastics and combinations thereof, and preferably is constructed of a woven nylon fabric.

Magnet holder 30 also may be adapted to be releasably attachable to another object, e.g., by affixing hook fasteners or loop fasteners on one side to be releasably attachable to corresponding loop fasteners or hook fasteners on the other object. In one example, the magnet holder 30 may be adapted to be releasably attachable to a portion of, most, substantially all, or even all of the harness 10 or comparable structure, such as the vest-like article of clothing 80 depicted in FIG. 12. This embodiment provides a virtually limitless number of positions at which the magnet holder 30 may be attached, which in turn provides a virtually limitless number of positions at which the users arm may be secured.

The magnet holder 30 may be placed at a desired position, such as inside a pocket or inside an article of clothing. A second magnet, such as the magnet 28 of strap 20 of FIG. 2 or the magnet 53 of strap 51 of FIGS. 9-10, may be positioned on the body part the movement of which is desired to be restrained and positioned in proximity to the magnet 38 of magnet holder 30. The attractive forces of the two magnets operate to releasably connect and thereby restrain the movement of the body part, without the use of a harness, such as harness 10 of FIG. 1. This embodiment is particularly advantageous where the user desires to limit the visibility of the restraint or requires periodic, more limited support, such as a Parkinson disease patient or a stroke victim who wishes to discreetly support an arm, without necessarily having to wear a larger, more visible support, such as the harness 10 of FIG. 1.

The relative strength of the magnetic devices to be employed in the present invention is dependent on the particular application, including the type of user. In general, the magnets should be of sufficient strength such that the attractive magnetic forces of two magnets together can restrain and/or support the body part at the desired location. Preferably, the magnets are of sufficient strength to allow one to intentionally release or pull them apart, while not releasing or pulling apart unintentionally, when at rest or during desired activities. For the application of immobilizing an upper arm, a desired activity preferably includes the used of the hand of that upper arm for certain activities. For the application of immobilizing a lower leg, a desired activity preferably includes the ability to move the upper leg from side to side to some extent.

Alternatively, magnetic devices of greater strength may be used to restrain one or more limbs, other body parts, or even an entire body such that the user is unable to release the restraint without assistance from another. Such applications can include restraining persons to prevent undesirable movement during medical procedures, public safety, apprehension by police, etc.

The attractive force between two magnets may be adjusted or fine tuned for a particular application by changing the type of material or by varying the thickness of the material covering each of the magnets. For example, since the attractive magnetic forces decrease as the distance between the magnets increases, utilizing a thicker material covering a magnet will effectively decrease the attractive force. In addition, or in the alternative, the relative attractive magnetic forces between two magnets may be decreased by decreasing the mass of a magnet, e.g., by decreasing the thickness of one or both magnets. This may be particularly advantageous for small or fragile persons, who may need or desire a relatively weaker magnetic force to be able to separate the magnets without assistance from another.

The magnets may be any of a variety of strengths, shapes, sizes and types. Also, the one or more magnets on the body part to be restrained and the one or more magnets positioned at the desired location of restraint may be of different relative strengths, shapes, sizes and types, or preferably, the magnets are substantially the same strength, size, shape and type.

In one embodiment of the invention of the invention, the two magnets are flat and circular shaped and are different diameters. This allows a limited amount of movement by the smaller diameter magnet within the larger area of the larger diameter magnet. Such an arrangement provides some give or cushion to allow some movement in response to outside forces before the attractive force between the two magnets is broken.

The relative attractive forces between two magnets must be of sufficient strength to counter the forces of shear and pull. In this application, shear generally refers to the forces of the arm being pulled down or away from the body, while pull refers to the forces to pull the magnets apart. Regardless of the relative size, shape, type and strength of either magnet, the relative attractive forces between the two magnets must be sufficient for the two magnets to be releasably secured, while countering the forces of shear and pull.

In a preferred embodiment, neodymium iron boron magnets of the same grade were utilized, which were round, approximately 1.50 inches in diameter and 0.1875 inches thick. With a capturing material, such as woven fabric, placing the two magnets approximately 0.060 inches apart, the magnets had a Gauss reading of approximately 1,436.8, a magnetic attraction of approximately 15.3 pounds and a repulsion of approximately 9.1 pounds. Testing the above magnets in twenty shear pull tests resulted in an average shear force of 8.1 pounds.

Additional testing demonstrated that thickness of the magnets has a greater relative impact on the strength of the attractive magnetic forces than the diameter of the magnets. For example, two round magnets, each approximately 1.00 inches in diameter and 0.1875 thick, placed 0.060 apart demonstrated a pull strength of 13.1 pounds, which was 2.2 pounds less than the similarly tested 1.50 inch diameter magnets above. In contrast, increasing the thickness of the magnets from 0.1875 inches to 0.250 inches, while leaving the other variables constant, resulted in a pull strength of 25.6 pounds. Similarly, increasing the thickness of the magnets to 0.375 inches, the pull strength further increased to 49.8 pounds. Preferably, the relative strength of the magnets is varied by changing the thickness of the magnets and/or changing the thickness of the spacing between the magnets.

Preferably, the immobilizer of the present invention employs two magnets having attractive magnetic forces. Alternatively, one magnet may be used, which may be releasably connected to a magnetic surface.

In the application of an arm immobilizer, a preferred embodiment for an average adult to releasably immobilize one arm in an elevated position on a portion of the torso, the magnets preferably have a magnetic attraction of approximately 15 pounds to approximately 30 pounds and a shear of approximately 8 pounds to approximately 15 pounds.

At least one magnet is secured on the body part desired to be restrained and/or supported and at least one magnet is secured at the desired location for the body part to be held. More than one magnet may be used, e.g., depending on the size, strength and/or type of magnets and the application. For example, three magnets may be secured at different positions along a leg of a person and be releasably attached to three corresponding magnets secured at a desired location, such as along the side of a hospital bed or along the side of a wheelchair. Preferably, one magnet is secured on the body part and may be releasably connected by attractive magnetic forces to one magnet secured at or near the desired location for the body part to be held.

In a preferred embodiment of an arm immobilizer, a strap is adapted to releasably attach to a desired location on the arm, preferably at or near the wrist area. The strap preferably comprises one magnet, as described above. The magnet on the arm strap may be aligned with, and temporarily, releasably attachable to, a magnet secured at the desired location, such as on the torso of the user.

Figure 5:
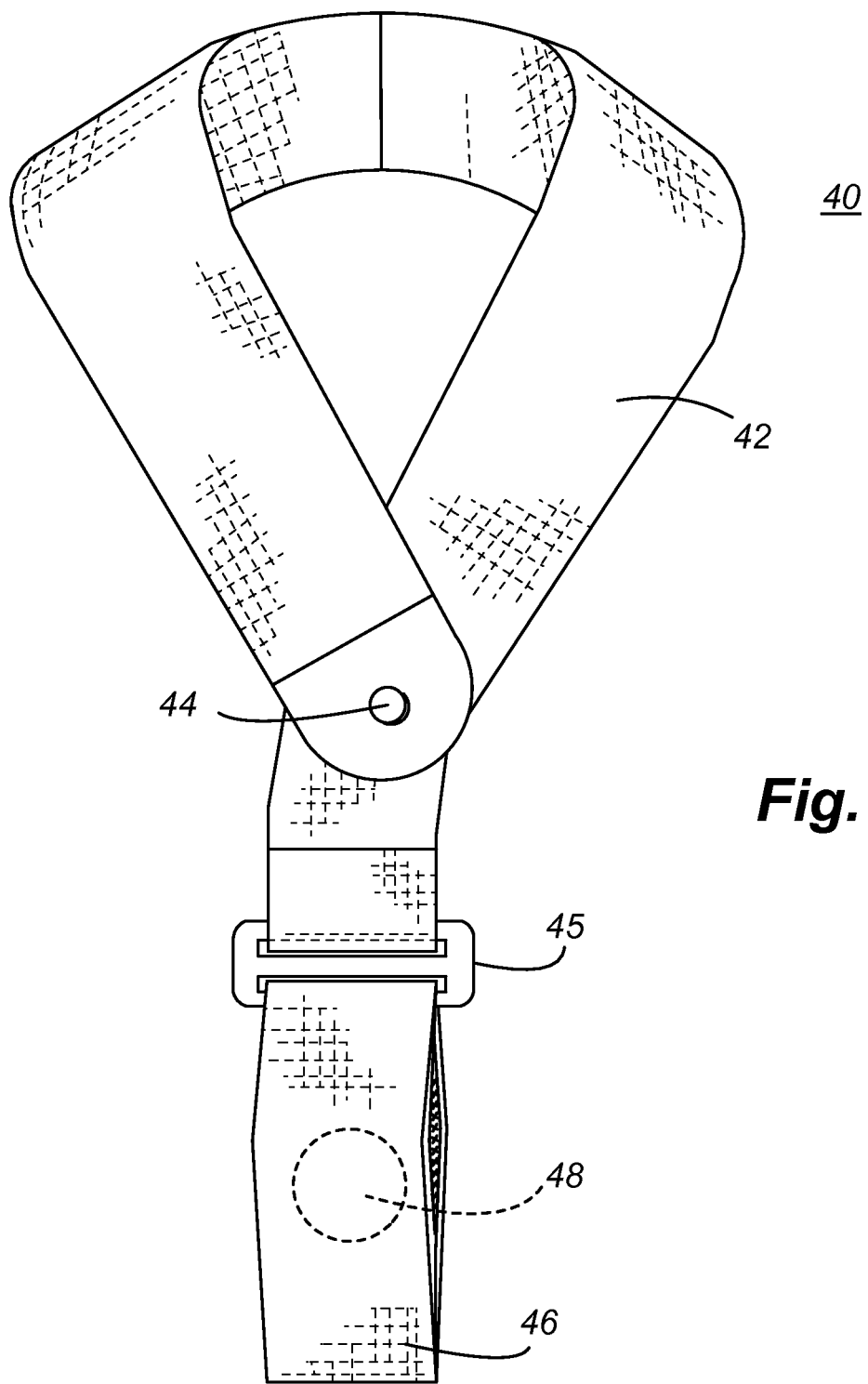
FIG. 5 depicts a front perspective view of another embodiment of the invention comprising a harness containing one or more magnetic devices.

Another embodiment of the invention is shown in FIG. 5. Harness 40 comprises a neck loop 42, one end of which is releasably attachable by connector 44 and a magnet holder 46 containing at least one magnet 48. Alternative embodiments may combine the neck loop 42 and the magnet holder 48 into a single piece. The harness 40 of FIG. 5 corresponds generally to the harness 10 of FIG. 1, but provides alternative features.

Neck loop 42 may itself contain one or more magnets, but preferably does not contain the one or more magnets. Rather, neck loop 42 preferably is connected to a magnet holder 46, which is adapted to contain one or more magnets 48. In the embodiment shown in FIG. 5, neck loop 42 is connected to one end of buckle 45, the other end of which is connected to magnet holder 46.

Magnet holder 46 is adapted to hold at least one magnet 48, and preferably is adapted to provide for the vertical and/or horizontal adjustment of the position of the magnet 48 relative to the harness 40. In the embodiment shown in FIG. 5, magnet holder 46 is a closed loop, which is one mechanism to allow the vertical adjustment of magnet 48. More preferably, the magnet holder 46 comprises hook and loop fasteners adapted to allow the vertical adjustment of magnet 48. For example, magnet holder 46 preferably comprises hook fasteners covering approximately one half of the length of the interior side of the closed loop, with loop fasteners covering approximately the other half of the length of the interior side of the closed loop. The magnet 48 preferably is positioned and held approximately in the middle of either one of the two halves. By releasing the hook and loop fasteners, the vertical position of the magnet 48 may thereby be adjusted upwards or downwards to a desired position and then secured at the position by re-connecting the hook and loop fasteners. Such a mechanism advantageously provides a multitude of vertical positions, while requiring but a single magnet 48 in magnet holder 46.

Alternatively, vertical and/or horizontal adjustment of the magnet relative to the harness, and thereby of the position of the arm to be immobilized, may be achieved by other means, such as securing more than one magnet in the magnet holder at predetermined positions, or by removing the magnet from its position and placing it at alternative positions, such as in open or closable sleeves within one or more portions of the harness.

The magnet holder 46 may be constructed of a variety of materials, such as natural fabrics, synthetic fabrics, plastics, and combinations thereof, and preferably is nylon fabric, with hook and loop fasteners, as described above. Preferably, the magnet holder 46 is approximately 2 inches to approximately 3 inches in width and approximately 14 inches to approximately 20 inches in length.

The magnet holder comprises sufficient structure to hold and secure at least one magnet. In another embodiment, the magnet holder comprises at least one open sleeve and/or at least one closable sleeve. By incorporating more than one such sleeve at various locations along the magnet holder, one may select from a variety of positions by moving a single magnet into a sleeve at a desired location. Preferably, the magnet or magnets are enclosed in material attached to, or a part of, the magnet holder, such as by being sewn-in. Preferably, material covers the magnet, so as to not allow direct metal-to-metal contact between a magnet of the harness and a magnet of the strap.

The strap is designed to hold or secure at least one magnet at a desired location, such as along an arm or leg. Preferably, the strap is a length of material designed to wrap around the arm or leg and be secured with a releasable fastener, such as a button, buckle, hook and loop fastener or similar device. More preferably, the length of strap may be adjustable to securely wrap around varying dimensions of arms and legs and be secured to the desired degree of snugness with the releasable fastener.

Figure 6:
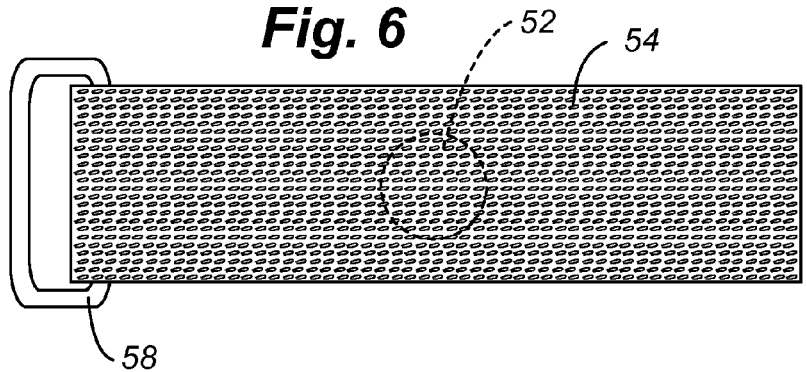
FIG. 6 depicts a front plan view of another embodiment of the invention comprising a strap containing one or more magnetic devices.
Figure 7:
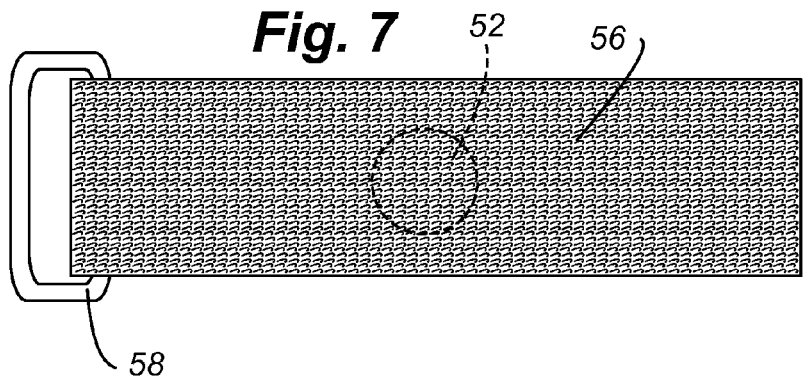
FIG. 7 depicts a back plan view of the strap depicted in FIG. 6.
Figure 8:
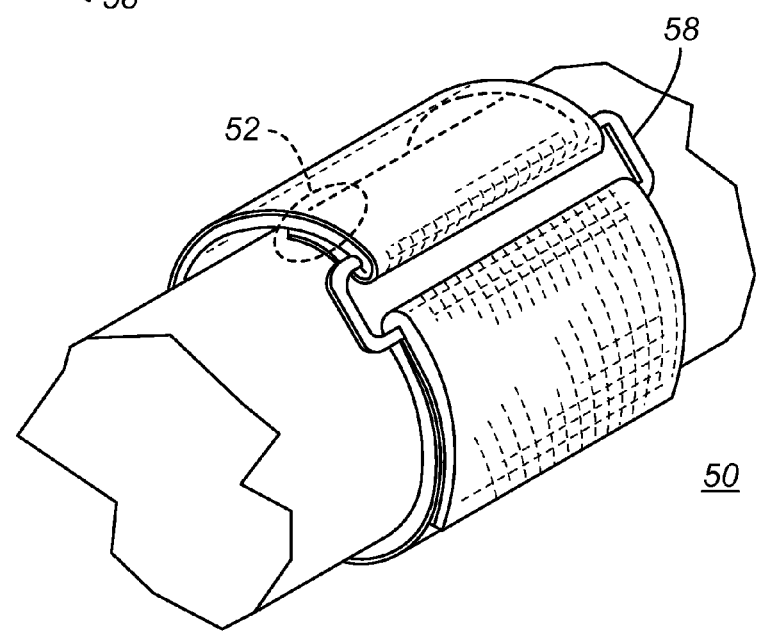
FIG. 8 depicts a perspective view of the strap depicted in FIGS. 6 and 7 as wrapped around an object.

In the embodiment shown in FIGS. 6-8, strap 50 containing magnet 52 comprises a first side having hook fasteners 54 along at least a portion of its length and a second side having loop fasteners 56 along at least a portion of its length. The strap 50 preferably comprises a loop 58 at one end, to allow the strap 50 to form a releasable, adjustable closed loop. As shown in FIG. 8, the end of the strap 50 not having the loop 58 may be threaded through loop 58, and doubled back onto the rest of the strap 50. The opposing hook 54 and loop 56 fasteners releasably secure the strap 50 at the desired position, thereby providing adjustability of the circumference of the strap 50 for a variety of applications.

Figure 9:
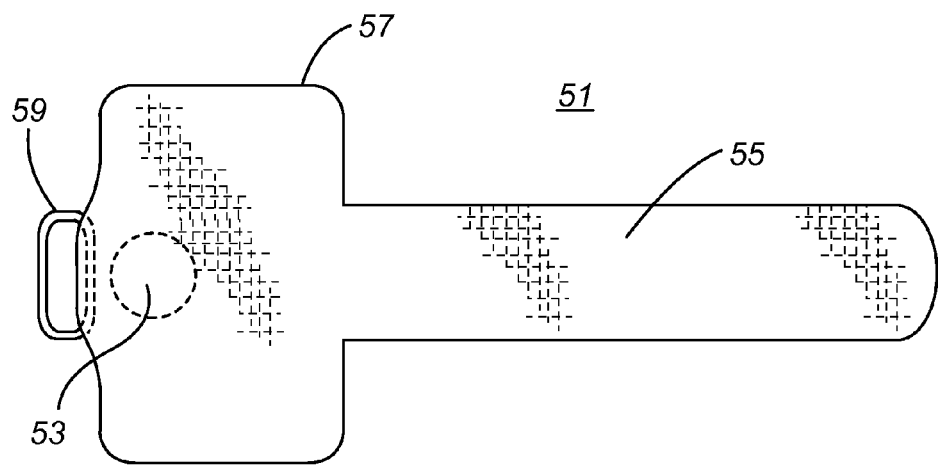
FIG. 9 depicts a front view of another embodiment of the invention comprising an alternative strap containing one or more magnetic devices.
Figure 10:
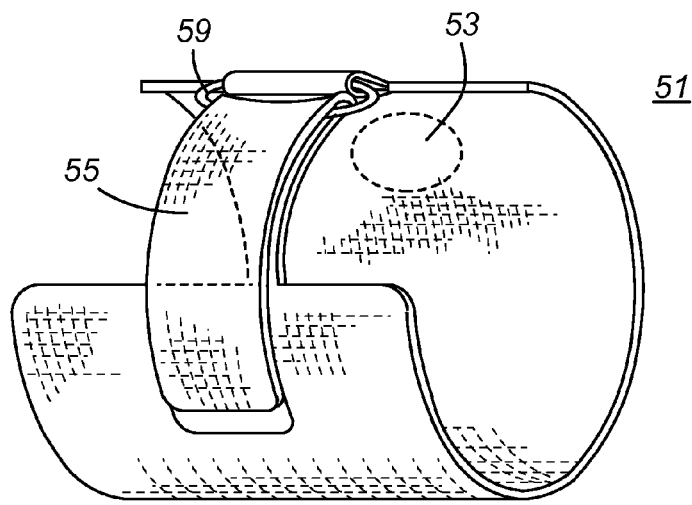
FIG. 10 depicts a perspective view of the strap depicted in FIG. 9 as wrapped around an object.

Another embodiment of the invention is shown in FIGS. 9 and 10, where the strap 51 comprises additional material for additional comfort to the user. Strap 51 comprises a length of material 55 having hook and loop fasteners on either side, similar to strap 50 of FIGS. 6 and 7, a loop 59, at least one magnet 53, and a piece of material 57, preferably wider than the length of material 55 and more preferably padded with foam material as well. As shown in FIG. 10, the strap 51 is releasably attachable to the portion of the body sought to be restrained by threading the end of the strap 51 through the loop 59 and doubling back onto the rest of the strap 51. Opposing hook and loop fasteners on length of material 55 releasably secure the strap 51 at the desired position, thereby providing adjustability of the circumference of the strap 51 for a variety of applications and preferably providing a wider, padded surface for additional comfort to the user.

Figure 11:
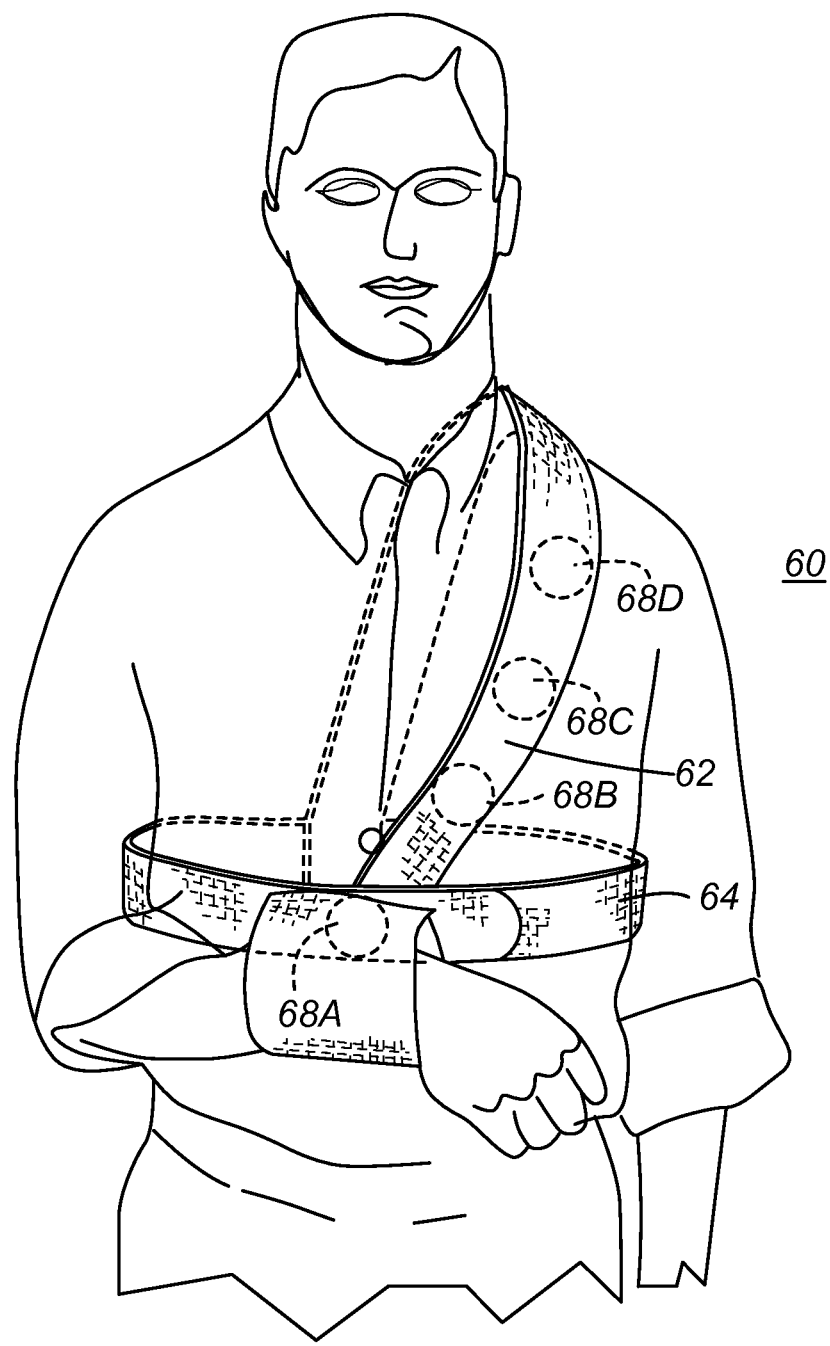
FIG. 11 depicts a front perspective view of another embodiment of the invention comprising a harness containing one or more magnetic devices and a strap as utilized by a person.

Another alternative embodiment of the invention is shown in FIG. 11. In this embodiment, harness 60 comprises at least one diagonally extending shoulder strap 62, waistband 64 and at least one magnet 68A-D. The waistband 64 is adapted to circumvate the torso, and preferably the waist area, of a person and preferably is releasably secured, such as by a buckle, button, snap, clip and more preferably with hook and loop fasteners and adjustable in length. Alternatively, the waistband 64 may be a closed loop, at least a portion of which is sufficiently elastic to hold the waistband in a desired location around the torso of the user.

The waistband 64 may be constructed of many types of materials, including cloth, leather, and webbing, and preferably is constructed of a woven elastic material, and more preferably a woven elastic material approximately 4 inches in width. Optionally, the waistband 64 may be adapted to receive and secure one or more magnets 68A and may be used with or without shoulder strap 62. Waistband 64 may further be adapted to provide a plurality of positions for one or more at least one magnet 68A at different positions, by adjusting the waistband 64 itself, or by providing a plurality of magnets spaced apart along waistband 64.

Shoulder strap 62 is adapted to secure one or more magnets in a desired location on the torso of the user. Referring again to FIG. 11, one embodiment of the invention comprises shoulder strap 62 with a first end and a second end, each connected to the waistband 64, forming a loop adapted to extend over the shoulder of the user. The synthetic fabrics, plastics, and combinations thereof, and preferably is a woven elastic fabric. The length of shoulder strap 62 may be fixed or preferably is adjustable, to accommodate torsos of different lengths, widths and breadths.

The shoulder strap 62 is adapted to secure at least one magnet 68B-D and may secure a series of magnets spaced apart to provide alternative positions for releasably attaching the corresponding attractive magnet on the wrist or leg. Optionally, the position of one magnet 68B, 68C and 68D may be adjusted relative to the waistband 64, e.g., by providing a plurality of open or closable sleeves in which to house one or more of magnets 68B-D at different positions or by adjusting the shoulder strap 62 itself.

The embodiment shown in FIG. 11 is intended for use in immobilizing the right arm of a user. An alternative embodiment (not shown) intended for immobilizing the left arm of a user would essentially be a mirror image of the harness 60 of FIG. 11. Yet another embodiment (not shown) comprises two shoulder straps, each similar to that of shoulder strap 62 of FIG. 11, one extending over each shoulder of the user. Such a harness could readily be utilized to restrain the movement of either the right arm or the left arm, or both arms.

Yet another embodiment of the invention comprises at least one shoulder strap comprising a length of material intended to wrap around the torso of the user and be secured with a releasable fastener, such as a button, buckle, hook and loop fastener or similar device. The shoulder strap comprises at least one magnet, but unlike the embodiments of FIG. 11, there is no waistband.

The shoulder strap is adapted to secure at least one magnet and may secure a series of magnets spaced apart to provide alternative positions for releasably attaching the corresponding attractive magnet on the wrist or leg. Preferably, the position of one magnet may be adjusted, e.g. by providing a plurality of open or closable sleeves in which to house the magnet at different positions. More preferably, the shoulder strap itself is adapted to provide a multitude of positions for the magnet, e.g., by rotating the shoulder strap about the torso of the user.

The user may releasably attach a strap containing at least one magnet onto a portion of the body part to be immobilized. In this embodiment, the strap (such as strap 50 depicted in FIGS. 6 and 7) is attached to the user's arm in the vicinity of the elbow, which immobilizes the upper portion of the user's arm, while allowing relative freedom of movement of the portion of the arm below the elbow. This method and apparatus may be particularly suitable for relatively minor, or partially healed, shoulder injuries.

Yet another embodiment of the invention is depicted in FIG. 12. An article of clothing 80 is adapted to receive and secure one or more magnets 86A-E at desired locations to releasably attach to a corresponding attractive magnet secured on the body part to be immobilized. The one or more magnets 86A-E may be received and secured by the article of clothing 80 through a variety of mechanisms, including an open sleeve, a closable sleeve, and an enclosure. In one embodiment, a single magnet may be used in a first position within the article of clothing for a desired purpose or time period and may be moved into one or more alternative positions, if desired. For example, a multitude of pockets or sleeves may be constructed and positioned at desired locations on the article of clothing, and a single magnet may be moved into a pocket or sleeve to provide the desired location. Preferably, each of the one or more magnets 86A-E is more securely positioned at specified locations in the article of clothing.

In a preferred embodiment, the article of clothing 80 comprises a vest adapted to receive and secure at least one magnet, preferably five magnets, 86A, 86B, 86C, 86D and 86E, spaced apart at desired locations. The magnets may be arranged in a variety of configurations, such as along a diagonal line like that of the diagonal shoulder straps in FIG. 10, or preferably in a vertical alignment, or both, or some combination thereof, or any other desired location. The article of clothing 80 optionally may comprise additional or alternative structure, such as a waistband.

The article of clothing 80 may be constructed of a variety of materials, such as natural fabrics, synthetic fabrics, plastics, and combinations thereof, and preferably is a lighter weight natural fabric, such as cotton. The article of clothing may be adapted to be worn as clothing, over the top of other clothing, or preferably under other clothing.

A variety of harness, straps and other magnet holders may be employed in various combinations. For example, the harness 10 of FIG. 1, the magnet holder 30 of FIG. 4, the harness 40 of FIG. 5, the harness 60 of FIG. 10, the harness 60 of FIG. 11, the article of clothing 80 of FIG. 12 and other alternative harnesses and magnet holders and magnet acceptors may be utilized with any or all of the strap 20 of FIG. 2, strap 50 of FIGS. 6-8 and other alternative straps and similar and other devices to hold the magnet at the desired location of restraint.

Also, a magnet, with or without a cover, may be attached to the person without a strap. In one embodiment where the user is to wear, or is wearing a cast, at least one magnet may be attached directly to the cast. The magnet on the cast may then be releasably attached by attractive magnetic forces to another magnet or magnetic material at a desired location, such as to a harness, strap or other magnet holder, or other surface, as described in several embodiments herein. Other embodiments may use other structures or other ways to attach or connect a magnet or a magnetic force to the part of the body desired to be restrained.

Figure 13:
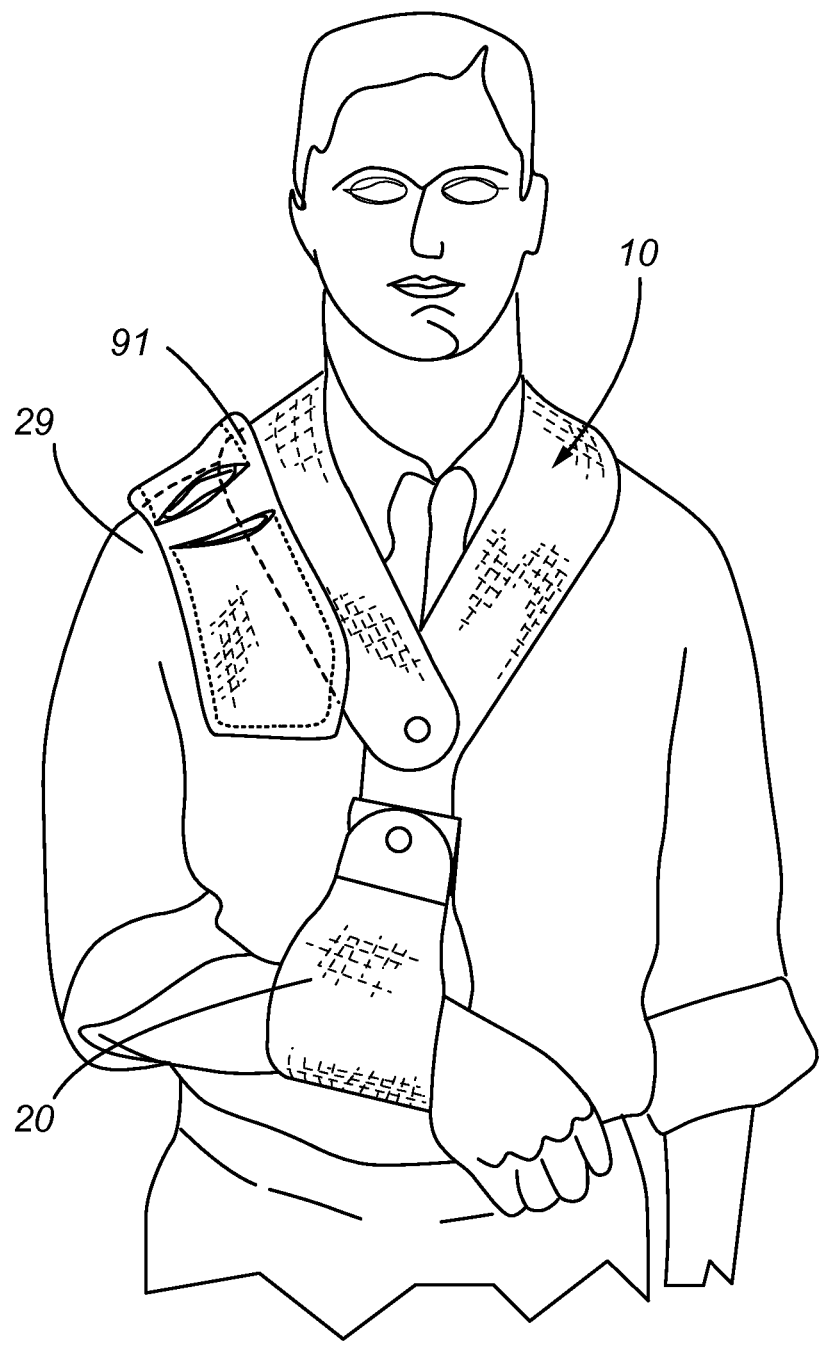
FIG. 13 depicts a front perspective view of yet another embodiment of the invention comprising a harness containing one or more magnetic devices, a therapeutic adaptation and a strap, as utilized by a person.
Figure 14:
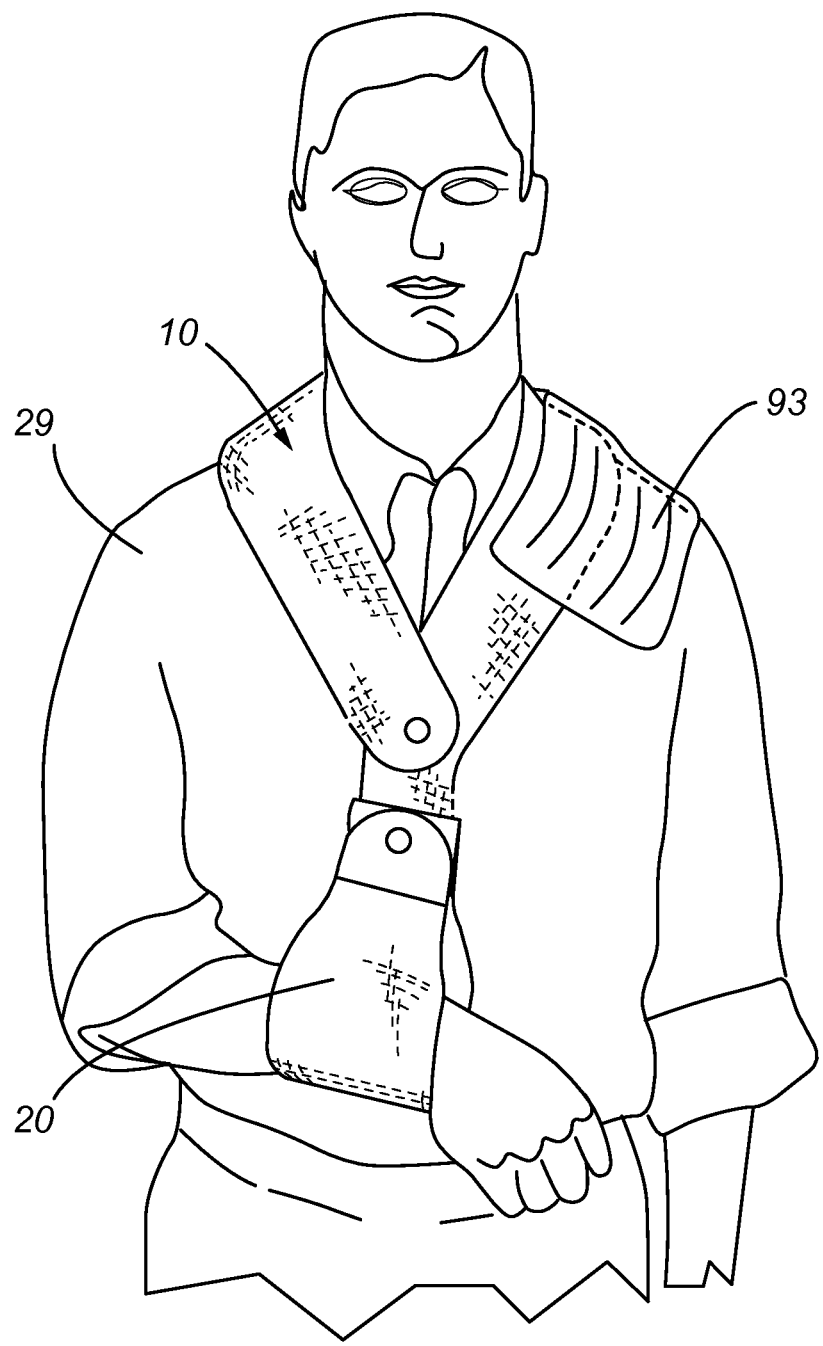
FIG. 14 depicts a front perspective view of yet another embodiment of the invention comprising a harness containing one or more magnetic devices, a therapeutic adaptation and a strap, as utilized by a person.

Additionally, it may be advantageous for the immobilizer to be adapted to provide therapeutic capabilities, such as heat or cold. One embodiment of the invention providing such therapeutic capabilities is shown in FIG. 13, where a user is wearing magnet holder 20 and harness 10, which is adapted to secure holder 91. Holder 91 is adapted to hold a hot pack or a cold pack at a desired position of the body of the user 29. Preferably, holder 91 comprises a open or readily openably sleeve into which a separate hot pack or a cold pack may be selectively inserted and removed as desired or prescribed. Holder 91 may be an integral part of harness 10, e.g., by being sewn onto harness 10 or by being a single piece, or preferably is releasably attachable to harness 10, such as with hook and loop fasteners. Even more preferably, the holder 91 comprises hook fasteners that are releasably attachable to loop fasteners along some, most, substantially all or all of harness 10. An alternative configuration of holder 91 is depicted in FIG. 14, where the holder 93 is sized and positioned to provide therapeutic capabilities, such as hot packs and cold packs to the user's collar bone and/or shoulder areas.

In yet another embodiment of the invention, attractive magnetic forces may be used to restrain the movement of other limbs, or of other parts of the body, or even of the entire body. In one application, at least one magnet is secured at a desired location on the body part to be restrained, such as by a strap as described above, a pocket or sleeve, or within another article, such as a shoe, sock, trousers, etc. At least one magnet is secured at a desired location at which the body part is to be restrained, such as a part of or attachment to a wheelchair, a part of or attachment to an article of furniture, a bed, a seat in an automobile, or any number of other movable or fixed structures or body parts. One advantageous use of this embodiment is the support and restraint of a leg at an elevated position to reduce swelling due to an injury and enhance healing.

In the embodiment of a wheelchair application, preferably a strap, like that shown in FIGS. 6-7, contains at least one magnet and is releasably attachable to the leg of the user by hook and loop fasteners. At least one magnet is positioned on the wheelchair at a desired location to correspond to a magnet on the strap, or alternatively a portion of the wheelchair is permanently or temporarily magnetized with a magnetic force attractive to the magnet of the strap. By the attractive magnetic forces, the user's leg may be temporarily, releasably immobilized.

There are circumstances in which the use of magnetic forces may not be optimal, desired or even possible, e.g., where the user has a pacemaker and electrical interference may be a problem. As an alternative to magnetic forces, the immobilizer of the present invention may comprise a first piece adapted to be positioned at a desired part of the body of a user, such as an arm or a leg, and a second piece adapted to be positioned at a desired position of restraint, such as another part of the user's body or another structure. The first piece and the second piece are adapted to be releasably connected to each other, such as by attractive magnetic forces, button, buckle, snap, hook and loop fastener, or similar device. Each of the embodiments of the invention described above, and as depicted in the drawings, may alternatively comprise connecting means between the two pieces other than, or in addition to, the attractive magnetic forces therein. In yet another embodiment, the two pieces described herein may be more permanently attached, e.g., by being sewn, stabled or otherwise connected together in a manner that is not as readily releasable, or even be non-releasable, e.g., by forming the two pieces into a single solitary piece.

The foregoing description of the present invention has been present for purposes of illustration and description. The description is not intended to limit the invention to the form disclosed therein. Consequently, variations and modifications commensurate with the above teachings, and the skill or knowledge of the relevant art, are within the scope of the present invention. The embodiment described herein is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A restraining device, comprising:
a first magnet;
a first magnet holder adapted to secure the first magnet and to be releasably attachable to a location on the body of a user;
a second magnet having an attractive magnetic force to the first magnet;
a second magnet holder adapted to secure the second magnet and to be releasably attachable to at least one of a second location on the body of a user and a structure other than the body of the user, wherein the second magnet holder comprises a strap adapted to extend across at least a portion of the torso of the body of the user and a waistband adapted to circumvent around the user's waist area; and
at least one of the first magnet holder and the second magnet holder comprising non-magnetic material to cover at least a portion of at least one of the first magnet and the second magnet.

2. The restraining device of claim 1, wherein the second magnet holder is adapted to secure at least a third magnet.

3. The restraining device of claim 1, wherein the location on the body of the user is at least a portion of an arm.

4. The restraining device of claim 1, wherein the second magnet holder is adapted to provide more than one location in which to secure the second magnet.

5. The restraining device of claim 1, wherein the second magnet holder is adapted to provide adjustment of the location of the second magnet relative to the body of the user.

* * * * *